US010853244B2

(12) United States Patent
Petti et al.

(10) Patent No.: US 10,853,244 B2
(45) Date of Patent: Dec. 1, 2020

(54) RANDOMLY WRITABLE MEMORY DEVICE AND METHOD OF OPERATING THEREOF

(71) Applicant: SANDISK TECHNOLOGIES LLC, Plano, TX (US)

(72) Inventors: Christopher Petti, Mountain View, CA (US); Srikanth Ranganathan, San Jose, CA (US)

(73) Assignee: SANDISK TECHNOLOGIES LLC, Addison, TX (US)

( * ) Notice: Subject to any disclaimer, the term of this patent is extended or adjusted under 35 U.S.C. 154(b) by 210 days.

(21) Appl. No.: 15/604,994

(22) Filed: May 25, 2017

(65) Prior Publication Data

US 2018/0157587 A1    Jun. 7, 2018

Related U.S. Application Data

(60) Provisional application No. 62/431,060, filed on Dec. 7, 2016.

(51) Int. Cl.
    *G06F 12/06* (2006.01)
    *G11C 13/00* (2006.01)
    *C12N 15/11* (2006.01)

(52) U.S. Cl.
    CPC ............ *G06F 12/06* (2013.01); *C12N 15/11* (2013.01); *G11C 13/0014* (2013.01); *G11C 13/0019* (2013.01); *C12N 2310/20* (2017.05); *G11C 13/004* (2013.01); *G11C 13/0069* (2013.01)

(58) Field of Classification Search
    CPC ...... G06F 12/06; G06F 12/00–12/0692; G06F 5/08; G11C 13/0069; G11C 13/0014; G11C 13/004; G11C 13/00–13/0019; C11C 13/0014; G06N 3/123; C12N 2310/20; C12N 15/11
    See application file for complete search history.

(56) References Cited

U.S. PATENT DOCUMENTS 5,915,167 A   6/1999 Leedy
6,881,994 B2  4/2005 Lee et al.
2004/0114445 A1  6/2004 Occhipinti et al.
2004/0217345 A1  11/2004 Boland et al.
2015/0133315 A1*  5/2015 Jacobson ............... C12N 15/70 506/2
2015/0261664 A1*  9/2015 Goldman ............... G06N 3/123 711/154
2016/0371434 A1* 12/2016 Strauss ................. G06N 3/123
2018/0002725 A1*  1/2018 Ganjam ................. C12Q 1/68

FOREIGN PATENT DOCUMENTS

WO    WO-2018152197 A1 *  8/2018  .......... C07K 14/005

OTHER PUBLICATIONS

Entry for "logical address" in the Free On-Line Dictionary of Computing, printed from foldoc.org/logical+address as p. 1/1, page last updated on Jan. 1, 2001. (Year: 2001).*
Difference between logical and physical address in operating system. https://techdifferences.com/difference-between-logical-and-physical-address.html, Sep. 21, 2016, printed as pp. 1/4-4/4. (Year: 2016).*
Kleinstiver et al. Nature Biotechnology, vol. 33, No. 12, pp. 1293-1298, published online Nov. 2, 2015, including p. 1/1 of Online Methods, pp. 1/11-11/11 of Supplementary Figures, pp. 1/1 of Supplementary Note 1, and pp. 1/5-5/5 of Supplementary Note 2. (Year: 2015).*
Addgene, "CRISPR/Cas9 Guide," https://www.addgene.org/crispr/guide/ (visited Apr. 18, 2017), 13 pages.
Yazdi, S.M.H.T., et al., "A Rewritable, Random-Access DNA-Based Storage System," www.nature.com/scientificreports, 10 pages, published Sep. 18, 2015.
Church, G. M., et al, "Next-Generation Digital Information Storage in DNA," Sciencexpress, http://www.sciencemag.org/content/early/recent_/ Aug. 16, 2012, 2 Pages, 10.1126/science.

* cited by examiner

*Primary Examiner* — Jennifer Dunston
(74) *Attorney, Agent, or Firm* — The Marbury Law Group PLLC

(57) ABSTRACT

A method of writing data to a DNA strand comprises cutting an address block of a selected address-data block unit of the DNA strand to form first and second DNA strings, and inserting a replacement address-data block that includes a replacement data segment between the first DNA string and the second DNA string to provide a rewritten DNA strand having valid address followed by valid data and an invalid address followed by invalid data.

6 Claims, 5 Drawing Sheets

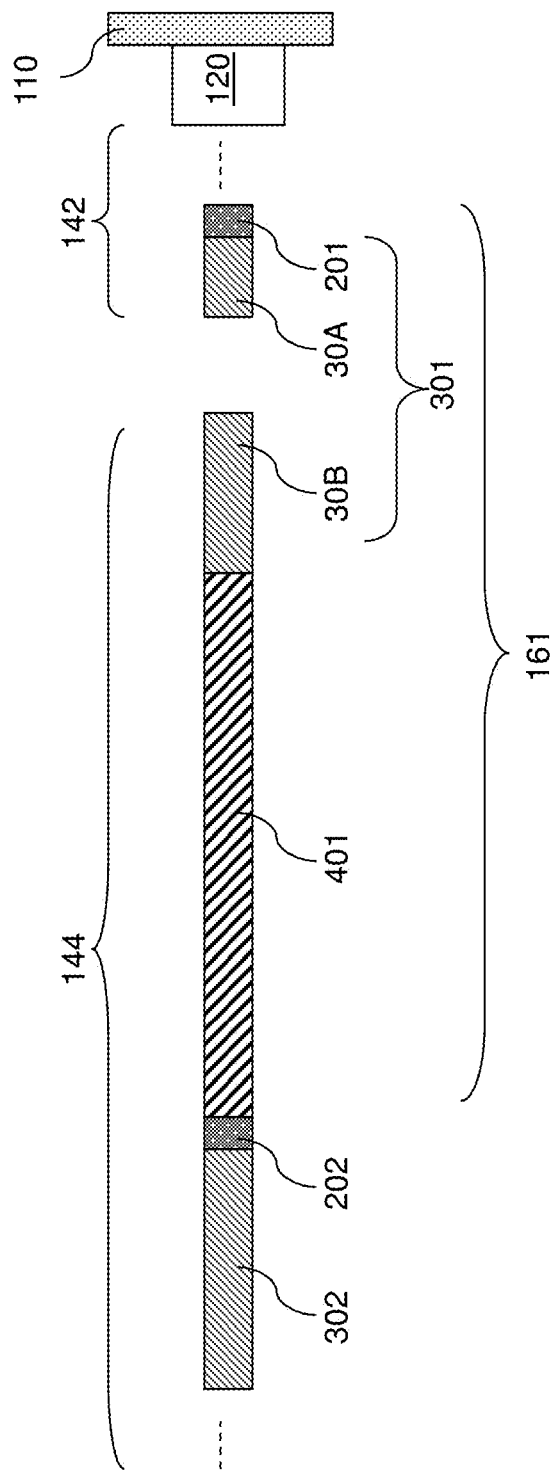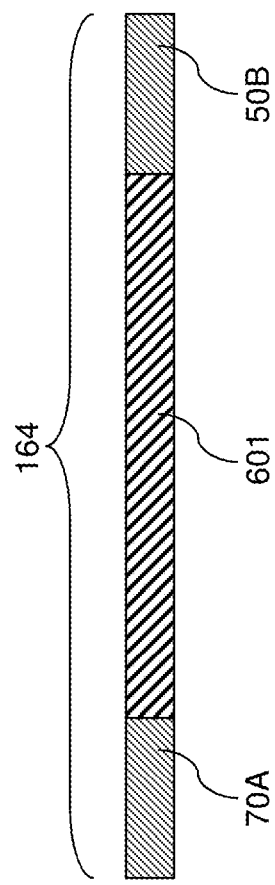

RANDOMLY WRITABLE MEMORY DEVICE AND METHOD OF OPERATING THEREOF

FIELD

The embodiments of the invention are directed generally to memory devices and methods of operating the same.

BACKGROUND

DNA memory can have a very large storage density. While semiconductor-based memory devices can provide memory density up to about $1.0 \times 10^{13}$ bytes/g, DNA-based memory devices can provide memory density up to about $1.0 \times 10^{20}$ bytes/g. Methods for coding/decoding data into DNA are known in the art. For example, to encode information in a DNA strand, an entire storage medium unit can be sequenced into a DNA strand, which may contain exabytes of information depending on the length of the DNA strand. To decode the information in the DNA strand, the entire medium must be sequenced. Random access of information in a DNA strand has been a challenge.

Various DNA based memory devices have been proposed. U.S. Patent Application Publication No. 2004/0217345 A1 to Boland et al., incorporated herein by reference in its entirety, discloses a DNA-based memory device in which information can be stored in a DNA strand that is affixed to a substrate via an anchoring compound. U.S. Patent Application Publication No. 2004/0114445 A1 to Occhipinti et al., incorporated herein by reference in its entirety, discloses a memory device employing DNA strand molecular switches and carbon nanotubes.

An addressing scheme in which individual segments of a DNA code can be identified by "address" sequences before and/or after the data blocks is disclosed in the article, Yadzi et al., A Rewritable, Random-Access DNA-Based Storage System, Nature, Scientific Reports 5, Article number: 16138 (2015), incorporated herein by reference in its entirety. The scheme by Yadzi employs a DNA-based storage architecture that enables random access to data blocks and rewriting of information stored at arbitrary locations within the blocks. Yadzi discloses the possibility of using a DNA string as a versatile media suitable for both ultrahigh density archival and rewritable storage applications.

However, Yadzi's scheme for accessing the data blocks and re-writing the data blocks requires the same cumbersome sequencing and expression techniques that are used to decode the entire DNA medium. For example, a polymerase chain reaction (PCR) amplification needs to be performed on the entire DNA medium in order to rewrite the DNA medium according to Yadzi's method.

SUMMARY

According to an aspect of the present disclosure, a method of writing data to a DNA strand, comprises providing a DNA strand including a sequence of address-data block units that are connected to one another, each of the address-data block units including a respective protospacer adjacent motif (PAM), a respective address block that identifies a logical address of the respective address-data block unit, and a respective initial data segment that includes stored data, cutting an address block of a selected address-data block unit within the DNA strand, wherein the address block is divided into an initial address portion within a first DNA string and a terminal address portion within a second DNA string, and inserting a replacement address-data block that includes a replica of the terminal address portion of the address block of the selected address-data block unit within the DNA strand, a replacement data segment, and an invalid initial address portion between the first and the second DNA strings to provide a rewritten DNA strand. A combination of the initial address portion and the replica of the terminal address portion provides a valid address block, and a combination of the invalid initial address portion and the terminal address portion provides an invalid address block that invalidates data stored in a subsequent initial data segment.

According to another aspect of the present disclosure, a method of reading data from a DNA strand which stores data comprises providing a DNA strand including a sequence of address-data block units that are connected to one another, each of the address-data block units including a respective protospacer adjacent motif (PAM), a respective address block that identifies a logical address of the respective address-data block unit, and a respective data segment that includes stored data, wherein at least one of the address-data block units comprises an invalid address block and an invalid data segment containing invalid data stored in a subsequent string of DNA sequences that follows the invalid address block, and wherein at least one other of the address-data block units comprises a valid address block and a valid data segment containing valid data stored in a subsequent string of DNA sequences that follows the valid address block. The method further comprises reading a sequence of the DNA strand employing a DNA sequence reader by reading a sequence of each valid data segment that follows the valid address block, and ignoring a sequence of each invalid data segment that follows an invalid address block until a next PAM is read by the DNA sequence reader.

According to yet another aspect of the present disclosure, a DNA strand memory device comprises a DNA strand that stores data and comprising a sequence of address-data block units that are connected among one another, each of the address-data block units including a respective protospacer adjacent motif (PAM), a respective address block that identifies a logical address of the respective address-data block unit, and a data segment that includes stored data, wherein at least one of the address-data block units comprises an invalid address block and an invalid data segment containing invalid data stored in a subsequent string of DNA sequences that follows the invalid address block.

BRIEF DESCRIPTION OF THE DRAWINGS

FIG. 2A is a schematic illustration of an intermediate structure derived from the randomly accessible DNA strand memory device of FIG. 1, which is obtained by cutting a location within an address block adjacent to a protospacer adjacent motif (PAM) according to an embodiment of the present disclosure.

FIG. 2B is schematic illustration of a DNA segment to be inserted between divided portions of the DNA strand of FIG. 2A according to an embodiment of the present disclosure.

DETAILED DESCRIPTION

Figure 1:
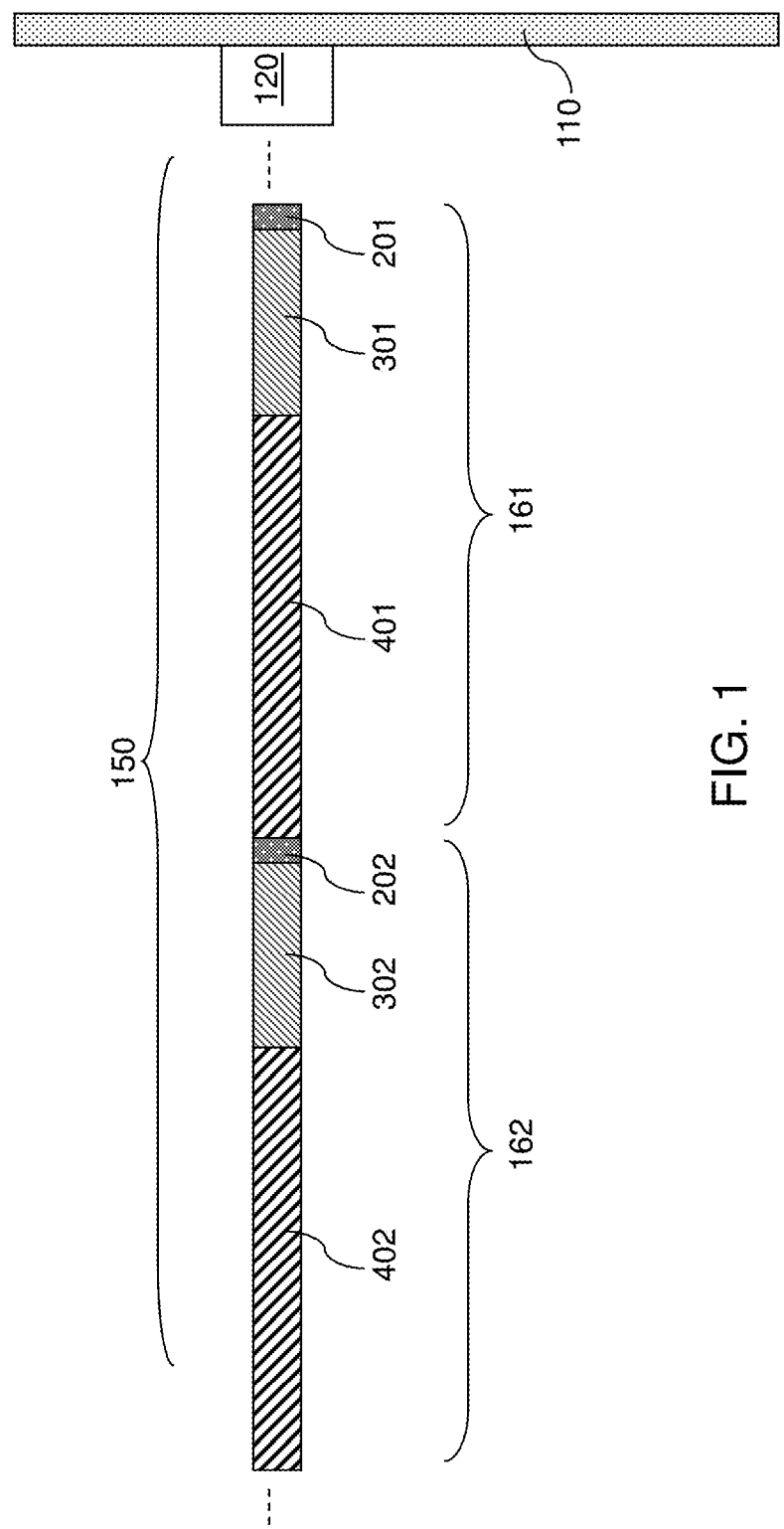
FIG. 1 is a schematic illustration of a structure of a randomly accessible DNA strand memory device using CRISPR/Cas protein accessing methods according to an embodiment of the present disclosure.

As stated above, the present disclosure is directed to randomly rewritable DNA memory devices by local gene sequence addition, and a method of operating the same, the various aspects of which are described below. Throughout the drawings, like elements are described by the same reference numeral. The drawings are not drawn to scale. Multiple instances of an element may be duplicated where a single instance of the element is illustrated, unless absence of duplication of elements is expressly described or clearly indicated otherwise. Elements with the same reference numerals are presumed to have the same composition and/or components unless expressly stated otherwise. Ordinals such as "first," "second," and "third" are employed merely to identify similar elements, and different ordinals may be employed across the specification and the claims of the instant disclosure.

Referring to FIG. 1, a first exemplary configuration for a randomly accessible DNA strand memory device is illustrated according to an aspect of the present disclosure. The DNA strand memory device employs at least one DNA strand 150 on which the memory address changes systematically, e.g., by increasing along the DNA strand 150, by decreasing along the DNA strand, or by otherwise changing in a pre-determined manner that allows systematic prediction of addresses based on location along each DNA strand.

The DNA strand memory device is randomly accessible employing a memory address identification scheme. For example, the randomly accessible DNA strand memory device can include at least one DNA strand 150 that includes a sequence of address-data block units (161, 162) that are connected to one another. By reading the addresses of address-data block units and bypassing data within unselected address-data block units (161, 162) during a read operation, data from a target address-data block unit can be read without reading data from any other address-data block. Thus, data in each address-data block can be individually, i.e., randomly, accessed without requiring reading of any additional data in an adjacent address-data block, thereby providing random access to the stored data. In one embodiment, each DNA strand 150 can be attached to a substrate 110 (e.g., a solid plate or bead) via a respective anchoring compound portion 120. The substrate 110 and the anchoring compounds portion 120 can include any material known in the art.

In one embodiment, each of the address-data block units (161, 162) can include a respective protospacer adjacent motif (PAM) (201, 202), a respective address block (301, 302) that identifies a logical address of the respective address-data block unit (161, 162), and a respective initial data segment (401, 402) that includes stored data for each address-data block unit (161, 162). Each DNA strand 150 can include a plurality of address-data block units (161, 162) that are attached among one another to provide the configuration of a single DNA strand. The number of address-data block units (161, 162) in each DNA strand 150 can be in a range from 2 to $10^{12}$, such as from $10^3$ to $10^9$, although a greater number of address-data block units (161, 162) can be provided per DNA strand 150.

The protospacer adjacent motif (PAM) (201, 202) can include about 3 base pairs (bps). An address block can include about 15-30 (such as 20) base pairs. A data segment includes as many base pairs as needed to contain stored data. The PAM (201, 202) is the same sequence for all address-data block units. In one embodiment, it can correspond to the specific Cas enzyme that will be used to access the storage medium, i.e., the DNA strand. For *Streptococcus pyogenes* Cas9, the PAM sequence is NGG. In one embodiment, the same PAM (201, 202) can be employed throughout the DNA strand 150. In another embodiment, different types of PAMs (201, 202) can be employed for a DNA strand 150 to access different regions of the DNA strand 150. Additionally or alternatively, different types of PAMs (201, 202) can be employed for different DNA strands 150 in order to access different DNA strands 150. In such cases, the variations in the PAMs (201, 202) can be employed to access different regions within a DNA strand 150 and/or to access different DNA strands 150. For example, different address-data block units in the DNA strand 150 include respective PAMs which are different from each other. In another example, the DNA strand memory device comprises plural DNA strands 150 comprising respective PAMs which are different from each other (e.g., a first strand contains a first PAM which is different from a second PAM in a second strand in the same device).

Different types of PAMs (201, 202) correspond to different Cas enzymes. Thus, different types of PAMs (201, 202) can be employed to delineate different categories of data. In one embodiment, different types of addresses can be tagged with different PAMs (201, 202). This approach can save access time.

The DNA-encoded information contained in each address-data block unit can be addressed by clustered regularly interspaced short palindromic repeats (CRISPR)/ CRISPR associated proteins (Cas) editing techniques. CRISPR is a genome editing tool that allows precision editing of genomes. CRISPR is a naturally-occurring DNA sequence in many bacteria that is repeated with unique sequences between the repeats. CRISPR is the first part of the bacteria's natural immune system. It is a library that keeps portions of dangerous viruses so that the bacteria can recognize and defend against those viruses next time they attack. Cellular apoptosis susceptibility (Cas) proteins are a set of enzymes that form the second part of the defense mechanism. A Cas protein can precisely snip DNA when a DNA sequence matches any of the unique sequences between a pair of CRISPR's. In an illustrative example, *Streptococcus pyogenes* have a CRISPR system that relies on the protein Cas9 as its Cas protein. The Cas9 endonuclease is a four-component system that includes two small RNA molecules, and enables snipping of DNA segments.

The CRISPR-Cas protein system is effective as a genome editing tool. The CRISPR-Cas protein system includes two molecules that introduce a change into the DNA. The first molecule is a Cas protein, which is an enzyme that functions as a pair of "molecular scissors" that can cut the two strands of DNA at a specific location. An example Cas protein (enzyme) is Cas9. The second molecule is a guide RNA (gRNA), which includes a small piece of pre-designed RNA sequence (about 20 bases long) located within a longer RNA scaffold. The scaffold part binds to DNA and the pre-designed sequence guides the Cas protein molecule to the right part of the genome. This self-aligning property ensures that the Cas protein enzyme cuts at the right point in the genome in the DNA strand. The guide RNA is designed to find and bind to a specific sequence in the DNA strand. The guide RNA has RNA bases that are complementary to those of the target DNA sequence in the genome. Thus, the guide RNA will only bind to the target sequence and no other regions of the genome in the DNA strand 150. The Cas protein can follow the guide RNA to a target location in the DNA sequence, and can make a cut across both strands of the DNA.

Each address block (301, 302) identifies the logical address of the respective address-data block unit (161, 162). In one embodiment, the memory device is an associative memory in which the addresses of valid address blocks (301, 302) on the DNA strand 150 are not required to have any specific order, such as a memory comprising a collection of key-value pairs or a large hash table. In another embodiment, addresses assigned to valid address blocks (301, 302) on the DNA strand 150 can strictly increase or strictly decrease from one end of the DNA strand 150 to another end of the DNA strand 150 (e.g., an address can be assigned a location corresponding to 0, 1, 2, 3, 4, etc.). Each initial data segment (401, 402) stores encoded data in the form of a respective DNA sequence therein.

In a method of rewriting data on a DNA strand 150, FIG. 1 corresponds to a first step in which a DNA strand 150 includes a sequence of address-data block units (161, 162) that are connected to one another. Each of the address-data block units (161, 162) includes a respective protospacer adjacent motif (PAM) (201 or 202), a respective address block (301 or 302) that identifies a logical address of the respective address-data block units (161 or 162), and a respective initial data segment (401 or 402) that includes stored data.

Referring to FIGS. 2A and 2B, and according to an aspect of the present disclosure, each DNA strand 150 within the randomly accessible DNA strand memory device of FIG. 1 may be edited to replace the data stored within any of the address-data block unit (161, 162) in the DNA strand 150. To replace data in a selected address-data block unit 161 shown in FIG. 2A with a replacement address-data block 164 shown in FIG. 2B, the DNA strand 150, including the selected address-data block unit 161, is cut at the address block 301 of the selected address-data block unit 161. The address block 301 is adjacent to a protospacer adjacent motif (PAM) 201 that is located employing the CRISPR-Cas protein scheme. The cutting (i.e., snipping or cleaving) of the DNA strand 150 occurs within the address block 301 of the selected address-data block unit 161 employing the Cas protein, such as Cas9 or Cas9 nickase.

Referring to FIG. 2B, a DNA segment is provided (e.g., prepared), which is a replacement address-data block 164. The replacement address-data block 164 includes the new data segment 601 (herein referred to as "replacement data segment") to replace the original data that is stored in the initial data segment 401 of the selected address-data block unit 161 that is cut (i.e., snipped or cleaved) into the first DNA string 142 and the second DNA string 144, as will be described in more detail below with respect to FIG. 3. The replacement address-data block 164 is designed to be inserted between divided portions (142, 144) of the DNA strand 150, i.e., between the first DNA string 142 and the second DNA string 144 shown in FIG. 2A.

The replacement address-data block 164 includes a partial address portion 50B that is a replica of the terminal address portion 30B of the cut address block 301, a replacement data segment 601 including the replacement data that replaces the data within the selected initial data segment 401, and an invalid initial address portion 70A. Preferably, the replacement address-data block 164 does not include a PAM. The invalid initial address portion 70A includes an address segment that, when combined with the terminal address portion 30B within the second DNA string 144 in a subsequent step, produces an invalid address. For example, the combination of the invalid initial address portion 70A and the terminal address portion 30B provide a partial (i.e., incomplete) address which is an invalid address. Thus, the replacement address-data block 164 can include, in order, a first address sequence that is the same as the sequence of the terminal address portion 30B of the second DNA string 142, the replacement data segment 601, and a second address sequence located at an opposite end of the first address sequence with respect to the replacement data segment 601 and including an invalid address portion. The invalid (e.g., partial) address portion provides the invalid address upon combination with the terminal address portion 30B of the second DNA string 144 in a subsequent step.

The first address sequence encoded in the partial address portion 50B is a portion of the replacement address (which is the same as the original address of the selected address-data block unit 161 for data rewrite operation) that will act as the right homology arm for subsequent binding to the first DNA string 142. The partial address portion 50B is a replica of (i.e., is identical to) the terminal address portion 30B. The second address sequence encoded in the invalid initial address portion 70A is an invalid address portion that generates an invalid address upon combination with the address portion of the terminal address portion 30B of the second DNA string 144. The DNA sequence at the end segment of the invalid initial address portion 70A may partially match the end segment of the initial address portion 30A on the first DNA string 142 so that the invalid initial address portion 70A of the replacement address-data block 164 can act as the left homology arm for subsequent binding to the second DNA string 144.

Figure 3:
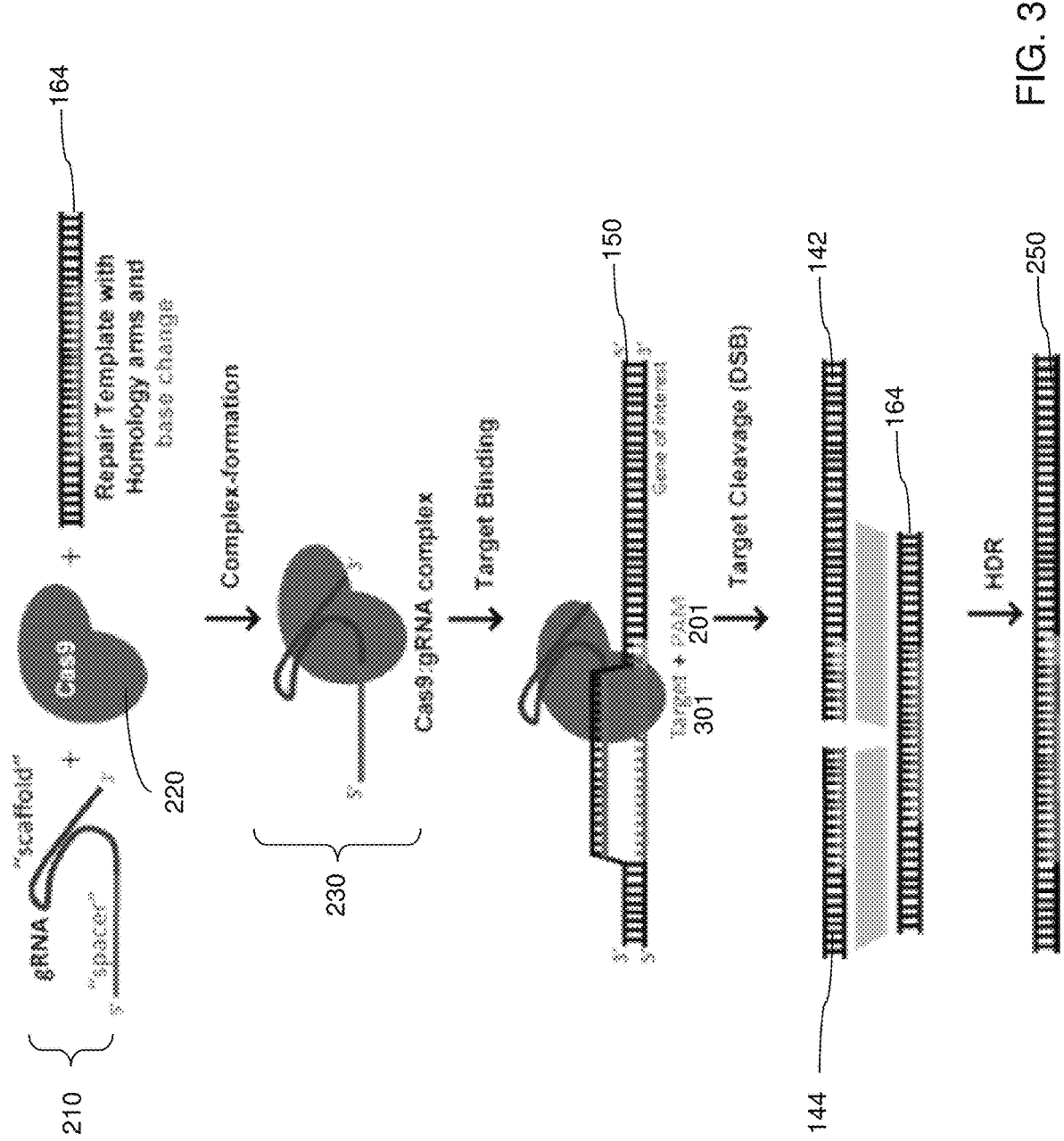
FIG. 3 is a schematic illustration of the homology directed repair (HDR) process according to an embodiment of the present disclosure.
Figure 4:
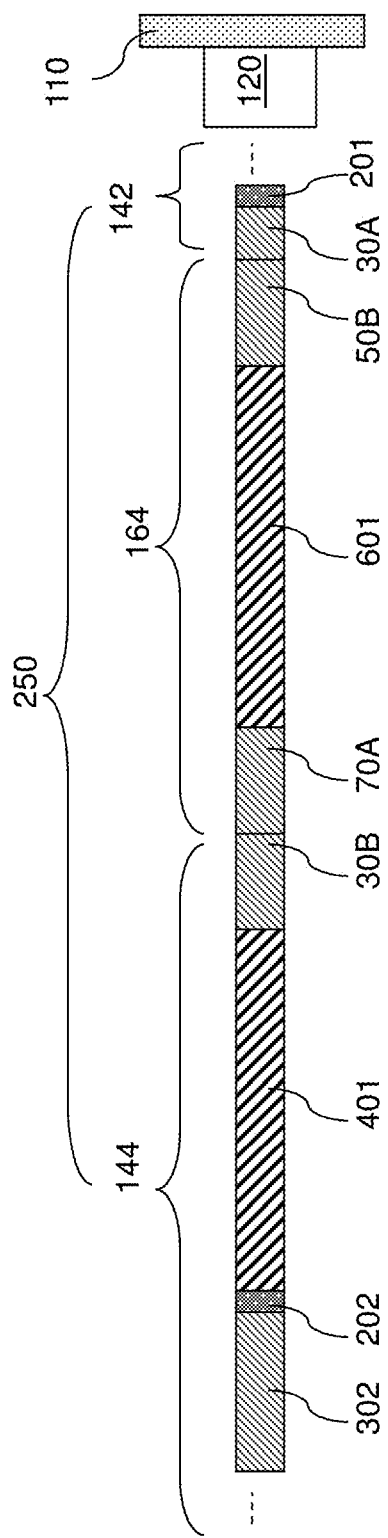
FIG. 4 is a schematic illustration of a re-written DNA strand memory device in a first exemplary configuration through insertion of an additional segment according to an embodiment of the present disclosure.

FIG. 3 illustrates an exemplary CRISPR based homology directed repair (HDR) process of one embodiment of the present disclosure which is used to cut (i.e., snip or cleave) the DNA strand 150 to form the first DNA string 142 and the second DNA string 144 and to insert the replacement address-data block 164 between the first DNA string 142 and the second DNA string 144 to form a rewritten DNA strand 250 shown in FIG. 4. Details of the HDR process are described in "CRISPR/Cas9 Guide" available at the website addgene.org, and are incorporated herein by reference in its entirety. In HDR terminology, the replacement address-data block 164 can be referred to as a "repair template".

As shown in FIG. 3, CRISPR includes "guide" RNA (gRNA) 210 and a non-specific CRISPR-associated enzyme (e.g., Cas9 endonuclease or Cas 9 nickase) 220. The gRNA is a short synthetic RNA composed of a "scaffold" sequence for Cas9 binding and a user-defined about 20 nucleotide "spacer" or "targeting" sequence which defines the genomic target to be modified. The gRNA 210 and the enzyme 220 are formed into a complex 230, as shown in FIG. 3. The repair template 164 and the complex 230 are delivered to the DNA strand 150. As described above, the repair template 164 contains the desired edit (i.e., the replacement sequence) as well as additional homologous sequence immediately upstream and downstream of the target (termed left and right homology arms). In other words, the repair template 164 includes the replacement sequence with a full address but no PAM on one end and a partial address on the other end, along with the Cas9 or Cas9 nickase enzyme. The enzyme finds the match to the address sequence it carries and binds to the DNA stand 150 at the target location (e.g., in address block 301) adjacent to the PAM 201. The enzyme 220 cuts (i.e., snips or cleaves) the DNA strand 150 at the target location (e.g., in address block 301) to form the first DNA string 142 and the second DNA string 144. Then, the repair template 164 is inserted via HDR between the first DNA string 142 and the second DNA string 144. HDR includes homologous (that is, the same base pair sequences) portions of oglionucleotides on both ends of the repair template 164. Thus, a portion of the address (e.g., partial address) of the address is located on the far end of the repair template.

In one embodiment, the Cas protein 220, such as Cas9, can be employed to find the "begin" address sequence within the selected address block 301. The begin address sequence of the selected address-data block unit 161 can be located by inducing relative movement between the Cas protein 220 of the complex 230 and the DNA strand 150. For example, a stochastic process may be employed in which the Cas9 protein searches for a target PAM. In one embodiment, the DNA strand 150 may move relative to the stationary Cas protein 220. In another embodiment, the Cas protein 220 may move relative to a stationary DNA strand 150. In yet another embodiment, both the DNA strand 150 and the Cas protein 220 move to enable "scanning" of the DNA strand 150 by the Cas protein 220.

Upon location of the PAM 201 and the selected address block 301 of the selected address-data block unit 161, a break (i.e., cut) in the DNA strand 150 can be made in the middle of the begin address sequence. The address block 301 of the selected address-data block unit 161 can be snipped employing the Cas protein (which may be, for example, Cas9 or Cas 9 nickase) 220 of the complex 230. In one embodiment, a double-strand break (DSB) may be employed to cut the address block 301 of the selected address-data block unit 161. Alternatively, a pair of single strand "nicks" can be employed to cut the address block of the selected address-data block unit 161.

The cut (i.e., snipped or cleaved) address block 301 is divided into an initial address portion 30A within a first DNA string 142 and a terminal address portion 30B within a second DNA string 144. The initial address portion 30A on the first DNA string 142 includes insufficient address for identifying a logical address therefrom. The terminal address portion 30B within the second DNA string 144 also includes insufficient address for identifying a logical address therefrom.

In the method of rewriting data on the DNA strand 150, FIG. 2A corresponds to a step in the method of FIG. 3 in which an address block 301 of a selected address-data block unit 161 of the DNA stand 150 is cut. The address block 301 is divided into an initial address portion 30A within a first DNA string 142 and a terminal address portion 30B within a second DNA string 144.

The method of forming an invalid the address formed by the combination of the invalid initial address portion 70A and the terminal address portion 30B may include any one of various data invalidation algorithms. In one embodiment, the combination of the invalid initial address portion 70A and the terminal address portion 30B may form a partial (i.e., incomplete) address. In one embodiment, the invalid address block (70A, 30B) contains an invalid (e.g., partial) address that violates an address encoding rule for a valid address for addressing data stored in the DNA strand memory device. In one embodiment, the invalid initial address portion 70A can include an invalidation indicator that renders invalid any full address that incorporates the invalidation indicator. In one embodiment, the address encoding rule includes a parity check rule, and the invalid address violates the parity check rule. Other data invalidation methods may be used instead of, or in addition to, the data invalidation methods described above.

In the method of rewriting data on the DNA strand 150, FIG. 2B corresponds to a step in the method of FIG. 3 in which a replacement address-data block 164 is prepared. The replacement address-data block 164 includes a replica 50B of the terminal address portion 30B, a replacement data segment 601 including the replacement data, and an invalid initial address portion 70A.

In the method of rewriting data on the DNA strand 150, FIG. 4 corresponds to the last step in the method of FIG. 3 in which the replacement address-data block 164 including the replacement data is inserted into the storage medium including the two segments, i.e., the first DNA string 142 and the second DNA string 144, of the original DNA strand 150 using HDR. The initial address portion 30A and the first address sequence in the partial address portion 50B can be combined to collectively provide the same address (i.e., a valid address, such as a full (i.e., complete) address) as the original address block 301 prior to the cut. The second address sequence in the invalid initial address portion 70A and the final address sequence in the terminal address portion 30B of the second DNA string 144 provide an invalid address.

The step of combining the replacement address-data block 164 with the first DNA string 142 and the second DNA string 144 generates a rewritten DNA strand 250. The combination of the initial address portion 30A and the replica 50B of the terminal address portion 30B provides a valid address. A combination of the invalid initial address portion 70A and the terminal address portion 30B provides an invalid address block that invalidates data stored in a subsequent string of DNA sequences, i.e., within the initial data segment 401 selected for rewriting by the new data provided in the replacement data segment 601. The physical structure of the initial data segment 401 remains in the rewritten DNA string 250. The new data stored in the replacement data segment 601 is valid data, and is validated by the valid address provided by the combination of the initial address portion 30A and the replica 50B. The old data stored in the initial data segment 401 selected for rewriting is invalid data, which is invalidated by the invalid address provided by the combination of the invalid initial address portion 70A and the terminal address portion 30B.

As shown in FIG. 4, the combination of the initial address portion 30A and the replica 50B of the terminal address portion 30B provides a valid address. A combination of the invalid initial address portion 70A and the terminal address portion 30B provides an invalid address block that invalidates data stored in a subsequent initial data segment 401.

In one embodiment, the entirety of the initial data segment 401 within the selected address-data block 161 remains within the rewritten DNA strand 250 as the invalidated data stored in the subsequent string of the DNA sequences that follows a PAM 201, a new address block (30A, 50B) that includes the initial address portion 30A and the replica 50B of the terminal address portion 30B, and the replacement data segment 601.

The address block that contains the valid address is followed by the initial data segment (402) or the replacement data segment (601) that contains valid data. After the writing operation is completed, a reading operation described in more detail below may be performed. Specifically, the reading operation includes reading a sequence of the initial data segment or the replacement data segment that contains valid data that follows the address block that contains the valid address by a DNA sequence reader, and ignoring a sequence of each invalidated initial data segment that follows an invalid address block until a next PAM is read by the DNA sequence reader.

Additional rewriting operations can be performed on the rewritten DNA strand 250 at least once. In this case, the second, third, and fourth steps described above can be performed multiple times to add multiple replacement address-data blocks, and to invalidate corresponding pre-existing data segments provided in the first step.

In one embodiment, the DNA strand 150 including the sequence of address-data block units (161, 162) can be attached to an anchoring compound 120 at, or before, the first step. The DNA strand 150 including the sequence of address-data block units (161, 162) can be detached from an anchoring compound 120 prior to the second step in order to facilitate snipping of the DNA strand 150. After the fourth step, the rewritten DNA stand 250 can be attached to the anchoring compound 120.

Figure 5:
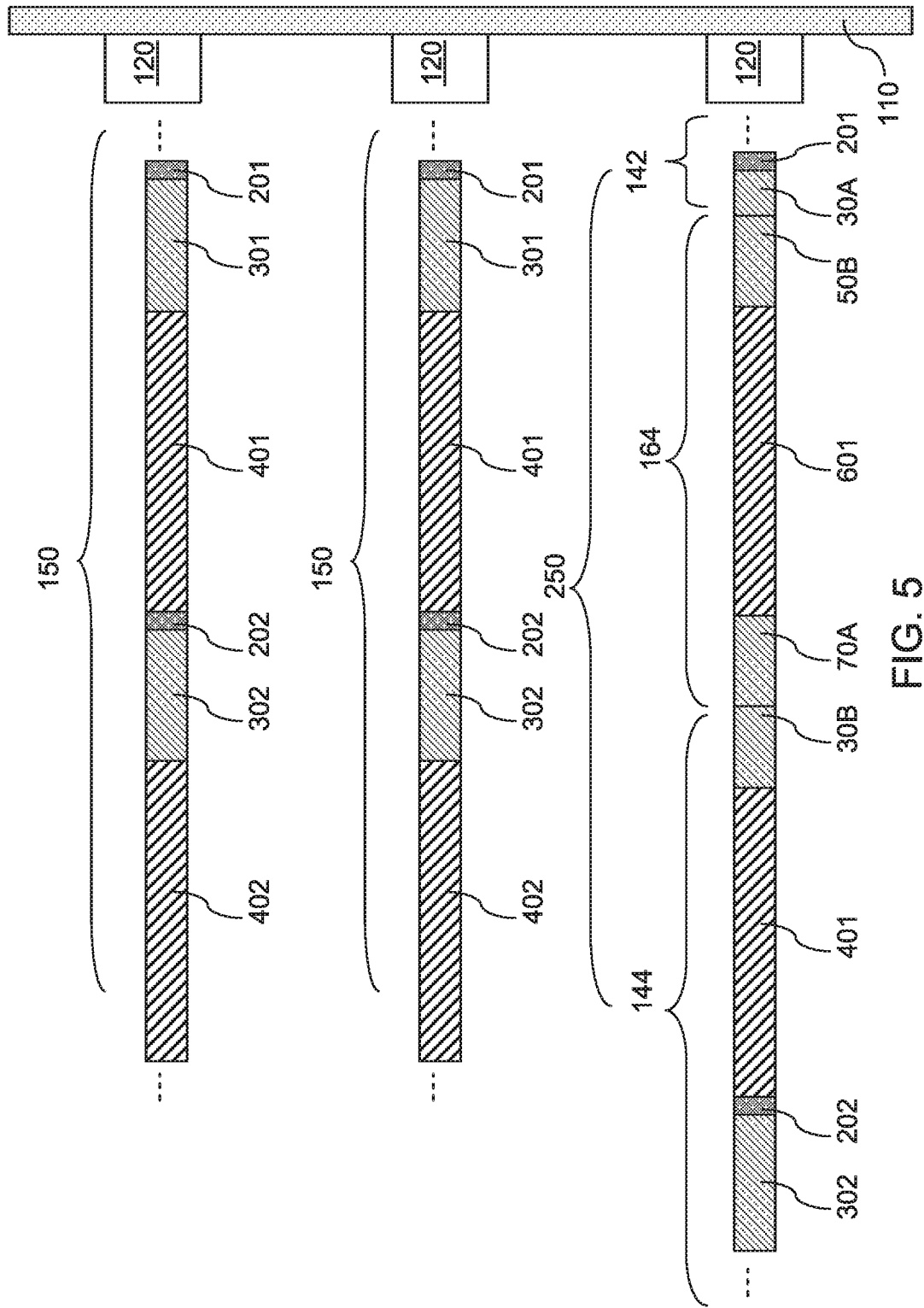
FIG. 5 illustrates a second exemplary configuration in which multiple DNA strands are attached to a common substrate in a DNA strand memory device according to an embodiment of the present disclosure.

Referring to FIG. 5, a second exemplary configuration for the randomly accessible DNA strand memory device of the present disclosure is illustrated. Multiple DNA strands (150, 250) are attached to a common substrate 110 through respective anchoring compounds 120 in the DNA strand memory device. Optionally, a protective medium (such as liquid, solid or gel) may be provided to protect the DNA strand memory device.

The methods of the present disclosure leave the old data in the medium (i.e., in the altered DNA strand). Thus, much of the medium volume (i.e., the DNA strand) can contain "junk" sections that do not include valid data after many writes. Occasionally, then, the entire medium can be re-sequenced, removing the junk areas (as tagged by invalid (e.g., incomplete) addresses).

According to an aspect of the present disclosure, the rewritten DNA strand 250 as modified by performing the second, third, and fourth steps multiple times can be re-sequenced by removing invalid address blocks and corresponding invalidated data. The re-sequencing may be performed by snipping the invalid data selectively while the randomly accessible DNA strand memory device is not in active operation, i.e., while the memory device is not accessed for recovery of stored data.

The method of inserting a new data sequence and invalid the old data by attaching an additional address string and by generating an invalid address block provides a faster mode of writing data into a DNA strand than re-writing the entire DNA strand, i.e., than the method of complete reassembly.

According to another aspect of the present disclosure, a DNA strand memory device comprising a DNA strand 250 that is configured to store data and comprising a sequence of address-data block units {(201, 30A, 50B, 601, 70A, 30B, 401), 162} that are connected among one another. Each of the address-data block units {(201, 30A, 50B, 601, 70A, 30B, 401), 162} includes a respective protospacer adjacent motif (PAM) (201 or 202), a valid (e.g., complete) respective address block {(30A, 50B), 302} that identifies a logical address of the respective address-data block unit {(201, 30A, 50B, 601, 70A, 30B, 401) or 162}, and a data segment {(601, 401), 402} that includes stored data. At least one (201, 30A, 50B, 601, 70A, 30B, 401) of the address-data block units {(201, 30A, 50B, 601, 70A, 30B, 401), 162} comprises an invalid address block (70A, 30B) and an invalid initial data segment 401 stored in a subsequent string of DNA sequences that follows the invalid address block (70A, 30B). At least another one 162 of the address-data block units {(201, 30A, 50B, 601, 70A, 30B, 401), 162} comprises a valid address block (30A, 50B) and an valid initial data segment 402 stored in a subsequent string of DNA sequences that follows the valid address block (30A, 50B).

In one embodiment, the invalid address block (70A, 30B) contains an invalid address that violates an address encoding rule for a valid address for addressing data stored in the DNA strand memory device. In one embodiment, the invalid address block (70A, 30B) is a partial (i.e., incomplete) address formed by the jointed portions 70A and 30B and the valid address block (30A, 50B) is a full (i.e., complete) address formed by the joined portions 30A and 50B. In one embodiment, the address encoding rule includes a parity check rule, the valid address satisfies the parity check rule, and the invalid address violates the parity check rule. In one embodiment, the invalid address block (70A, 30B) comprises a combination of an invalid initial address portion 70A that includes an invalidation indicator and a terminal address portion 30B. The invalidation indicator renders invalid any full address that incorporates the invalidation indicator.

In one embodiment, the sequence of address-data block units {(201, 30A, 50B, 601, 70A, 30B, 401), 162} can be attached to an anchoring compound 120 located on a substrate 110. In one embodiment, a plurality of additional DNA strands 150 may be attached to the substrate 110 through a respective anchoring compound 120.

According to another aspect of the present disclosure, a method of reading data from a DNA strand configured to store data is provided. A DNA strand 250 is provided, which includes a sequence of address-data block units {(201, 30A, 50B, 601, 70A, 30B, 401), 162} that are connected among one another. Each of the address-data block units {(201, 30A, 50B, 601, 70A, 30B, 401), 162} includes a respective protospacer adjacent motif (PAM) (201 or 202), a respective valid address block {(30A, 50B), 302} that identifies a logical address of the respective address-data block unit {(201, 30A, 50B, 601, 70A, 30B, 401) or 162}, and a data segment {(401, 601) or 162} that includes stored data. At least one (201, 30A, 50B, 601, 70A, 30B, 401) of the address-data block units {(201, 30A, 50B, 601, 70A, 30B, 401), 162} comprises an invalid address block (70A, 30B) and invalid data segment 401 stored in a subsequent string of DNA sequences that follows the invalid address block (70A, 30B).

A sequence of the DNA strand 250 can be read employing a DNA sequence reader. A sequence of each data segment (601, 402) that follows a valid address block {(30A, 50B, 302) that includes a respective valid address is read as valid data, i.e., providing valid data. A sequence of each data segment 401 that follows an invalid address block (70A, 30B) that includes a respective invalid address is ignored until a next PAM 202 is read by the DNA sequence reader.

The sequence of the DNA strand 250 can be read by any suitable DNA reading method. For example, in one embodiment, the DNA strand 250 is copied (e.g., first copied to form a complementary strand, which is again copied to provide a copy of the original DNA strand 250). The re-copying of the DNA can be performed to reconstruct a copy of the original DNA strand. Alternatively, since the original DNA strand and the first copied DNA strand are complementary, the first copied DNA strand can be read and the sequence of the original DNA can be determined without additional recopying of the first copied DNA strand. The copied DNA strand is chopped into pieces, and one or more pieces of interest are read using the valid address block as a primer. After reading, the one or more pieces of the copied DNA strand are discarded.

In another embodiment, a piece of interest of the DNA stand 250 (e.g., a piece that follows the valid address block which is used as a primer) is copied and amplified, using a suitable technique, such as PCR. The amplified copies are read and then discarded.

In one embodiment, each invalid address block (70A, 30B) includes an invalid initial address portion 70A and a terminal address portion 30B. The invalid initial address portion 70A includes an invalidation code that identifies each address block (70A, 30B) including the invalidation code as an invalid address block irrespective of contents within the terminal address portion 30B.

Although the foregoing refers to particular preferred embodiments, it will be understood that the invention is not so limited. It will occur to those of ordinary skill in the art that various modifications may be made to the disclosed embodiments and that such modifications are intended to be within the scope of the invention. Where an embodiment employing a particular structure and/or configuration is illustrated in the present disclosure, it is understood that the present invention may be practiced with any other compatible structures and/or configurations that are functionally equivalent provided that such substitutions are not explicitly forbidden or otherwise known to be impossible to one of ordinary skill in the art.

What is claimed is:

1. A DNA strand memory device comprising a DNA strand comprising a sequence of address-data block units that are connected among one another, each of the address-data block units including a respective protospacer adjacent motif (PAM), a respective first DNA sequence that functions as a respective address block that encodes an address of the respective address-data block unit, and a respective second DNA sequence that functions as a respective data segment that includes stored data, wherein at least one of the address-data block units further comprises a third DNA sequence that functions as an invalid address block that is attached to the respective second DNA sequence, and further includes a fourth DNA sequence that is attached to the third DNA sequence and functions as an invalid data segment, wherein:
   only one PAM is provided for each of the address-data block units;
   each of the address-data block units begins with the respective PAM; and
   the invalid address block comprises a partial address, an invalidation indicator or DNA that violates a parity check rule.

2. The DNA strand memory device of claim 1, wherein the invalid address violates the parity check rule.

3. The DNA strand memory device of claim 1, wherein the sequence of address-data block units is attached to an anchoring compound located on a substrate.

4. The DNA strand memory device of claim 1, wherein different address-data block units in the DNA strand include respective PAMs which are different from each other.

5. The DNA strand memory device of claim 1, wherein the DNA strand memory device comprises plural DNA strands comprising respective PAMs which are different from each other.

6. The DNA strand memory device of claim 1, wherein at least another one of the address-data block units consists of the respective PAM, the respective first DNA sequence, and the respective second DNA sequence.

* * * * *